(12) United States Patent
Umbach

(10) Patent No.: US 12,036,370 B2
(45) Date of Patent: *Jul. 16, 2024

(54) HIATAL HERNIA TREATMENT

(71) Applicant: Thomas Umbach, Las Vegas, NV (US)

(72) Inventor: Thomas Umbach, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,422

(22) Filed: Feb. 8, 2023

(65) Prior Publication Data

US 2023/0181867 A1 Jun. 15, 2023

Related U.S. Application Data

(60) Division of application No. 17/033,359, filed on Sep. 25, 2020, now Pat. No. 11,596,762, which is a continuation of application No. 15/963,491, filed on Apr. 26, 2018, now Pat. No. 10,786,647.

(51) Int. Cl.
*A61M 19/00* (2006.01)

(52) U.S. Cl.
CPC .................................. *A61M 19/00* (2013.01)

(58) Field of Classification Search
CPC ........... A61B 2017/00575; A61B 2017/00743; A61B 2017/00818; A61B 2017/00827; A61B 17/00; A61B 17/00234; A61B 17/0057; A61B 17/04; A61B 17/064; A61M 19/00; A61M 2210/1053; A61M 2202/048; A61M 5/14; A61M 2210/1014; A61M 2210/1042; A61M 2210/105; A61F 2/0063; A61F 2/02; A61F 2/04; A61F 2002/044; A61F 2002/045

See application file for complete search history.

(56) References Cited

U.S. PATENT DOCUMENTS

| | | | | |
|---|---|---|---|---|
| 4,269,222 A | * | 5/1981 | Palti ..................... | A61M 5/1411 |
| | | | | 137/433 |
| 5,316,543 A | * | 5/1994 | Eberbach .............. | A61F 2/0063 |
| | | | | 128/897 |
| 6,960,233 B1 | * | 11/2005 | Berg ....................... | A61F 2/04 |
| | | | | 623/23.64 |
| 9,492,261 B2 | * | 11/2016 | Cohen .................... | A61B 17/06 |
| 10,786,647 B2 | * | 9/2020 | Umbach ............... | A61M 19/00 |
| 2003/0139803 A1 | * | 7/2003 | Sequin .................... | A61F 2/915 |
| | | | | 623/1.11 |
| 2017/0100331 A1 | * | 4/2017 | Klein ................... | A61K 31/167 |

OTHER PUBLICATIONS

Bell et al., Randomized double-blind placebo-controlled study of the efficacy of continuous infusion of local anesthetic to the diaphragm closure following laparoscopic hiatal hernia repair, Mar. 22, 2012, Surg Endosc, 26:2484-2488 (Year: 2012).*

* cited by examiner

*Primary Examiner* — Kevin C Sirmons
*Assistant Examiner* — Alexandra Lalonde
(74) *Attorney, Agent, or Firm* — Brownstein Hyatt Farber Schreck, LLP

(57) ABSTRACT

An improved hiatal hernia treatment enhances recovery after surgery by reducing a patient's pain at an area of treatment. The area of treatment contains the hiatal hernia and must be extensively divided before the hiatal hernia can be treated. The improved hiatal hernia treatment reduces the patient's pain through directed application of an anesthetic via an applicator positioned within the area of treatment. The reduction of the patient's pain increases the patient's comfort, reduces the need for pain medication, and lowers the patient's blood pressure to enhance recovery.

13 Claims, 4 Drawing Sheets

HIATAL HERNIA TREATMENT

CROSS-REFERENCE TO RELATED APPLICATION

This application is a division of U.S. patent application Ser. No. 17/033,359, filed Sep. 25, 2020, which is a continuation of U.S. patent application Ser. No. 15/963,491, filed Apr. 26, 2018.

BACKGROUND OF THE INVENTION

Field of the Invention

The invention relates to hernia procedures and in particular to an improved hiatal hernia treatment.

Related Art

Hiatal hernias can cause acid reflux, difficulty swallowing, regurgitation, and pain. In addition, vomiting and gastrointestinal bleeding can occur. Though small hiatal hernias may have some symptoms, large hiatal hernias can be serious and require surgery. For example, a hiatal hernia having limited blood flow may need to be treated through surgery.

From the discussion that follows, it will become apparent that the present invention addresses the deficiencies associated with the prior art while providing numerous additional advantages and benefits not contemplated or possible with prior art constructions.

SUMMARY OF THE INVENTION

An improved hiatal hernia treatment is disclosed herein. As will be described further below, the improved hiatal hernia treatment enhances recovery after surgery by directly addressing pain caused by a hiatal hernia treatment. The reduction in pain reduces the need for pain medication, increases patient comfort, and health during the postoperative recovery period.

In one exemplary method, a method for a hiatal hernia treatment is provided, with such method comprising exposing an area of repair containing a hiatal hernia, positioning one or more applicators at a hiatus within the area of repair, and applying an anesthetic at distinct portions of the hiatus with the applicator without pressurization. For example, the application of anesthetic may be gravity driven.

The method may also include adjusting a valve of the applicators, such as to control a flow of anesthetic. A nozzle of the applicators may be adjacent the hiatus when the anesthetic is applied. In addition, the nozzle of the applicators may be within the hiatus when the anesthetic is applied. Anesthetic may be applied to a portion of a diaphragm within the area of repair, to a portion of an esophagus within the area of repair, or both.

In another exemplary method, a method for a hiatal hernia treatment comprises exposing an area of repair containing a hiatal hernia, and positioning one or more applicators at a hiatus. The applicators comprise a reservoir holding anesthetic and one or more valves.

A flow of the anesthetic from the reservoir is provided when the valves are opened. The flow of anesthetic is applied to distinct portions proximate the hiatus with the applicators. The flow of anesthetic is gravity driven. The area of repair may be closed subsequent application of the flow of anesthetic.

A nozzle of the applicators may be adjacent the hiatus when the anesthetic is applied. In addition, the nozzle of the applicators may be within the hiatus when the anesthetic is applied. It is noted that the anesthetic may be applied to a portion of a diaphragm within the area of repair, to a portion of an esophagus within the area of repair, or both.

In another exemplary method, a method for applying anesthetic to a surgical incision is provided, with such method comprising exposing an area of repair of a patient, the area of repair encompassing the surgical incision, positioning one or more applicators at the area of repair, and applying the anesthetic to at least two distinct areas proximate the surgical incision.

The anesthetic is driven through the applicators substantially without pressurization. It is noted that the surgical incision may be sutured prior to the application of the anesthetic. In addition, the area of repair subsequent application of the anesthetic.

A nozzle of the applicators may be adjacent the surgical incision when the anesthetic is applied. In addition, the nozzle of the applicators may be within the surgical incision when the anesthetic is applied. The applicators may comprise a reservoir and one or more valves. The anesthetic may flow from the reservoir and through the applicators when the valves are opened.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

The improved hiatal hernia treatment herein is advantageous for patient recovery. A significant amount of tissue dissection occurs during a hiatal hernia repair treatment. This is because such tissue must be dissected in order to access the area of repair. The improved hiatal hernia treatment anesthetizes the area of repair to reduce pain and enhance recover after the treatment is completed.

Figure 1:
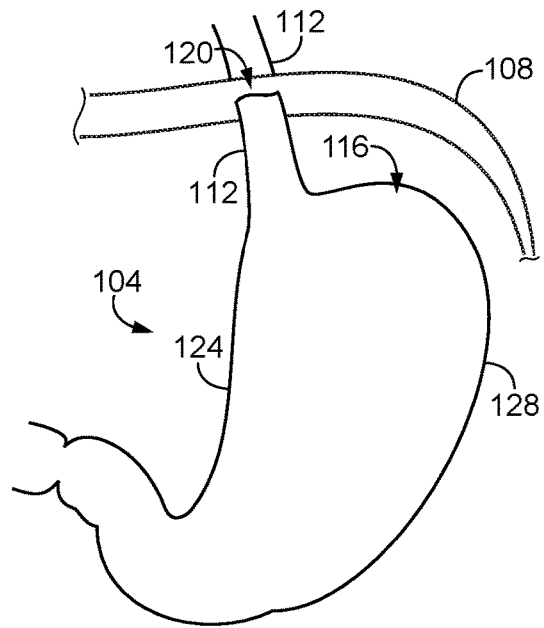
FIG. 1 is an anterior view of an exemplary abdominal region of a patient in a normal condition.

FIG. 1 illustrates an anterior view of an exemplary abdominal area in a normal condition. The esophagus 112 is shown extending through the diaphragm 108 to the stomach 104 via the hiatus 120. The stomach 104 comprises a fundus 116, a lesser curve 124, and a greater curve 128. As can be seen, the greater curve 128 at the fundus 116 forms a generally acute angle where the greater curve meets the esophagus 112 in a normal condition. In addition, the esophagus 112 extends through the diaphragm 108 via the hiatus 120 to the stomach 104 below in a normal condition.

Figure 2:
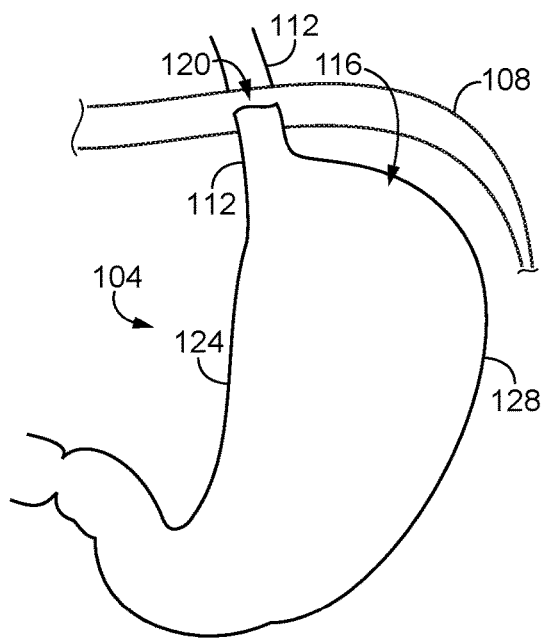
FIG. 2 is an anterior view of an exemplary abdominal region of a patient in an early stage condition.
Figure 3:
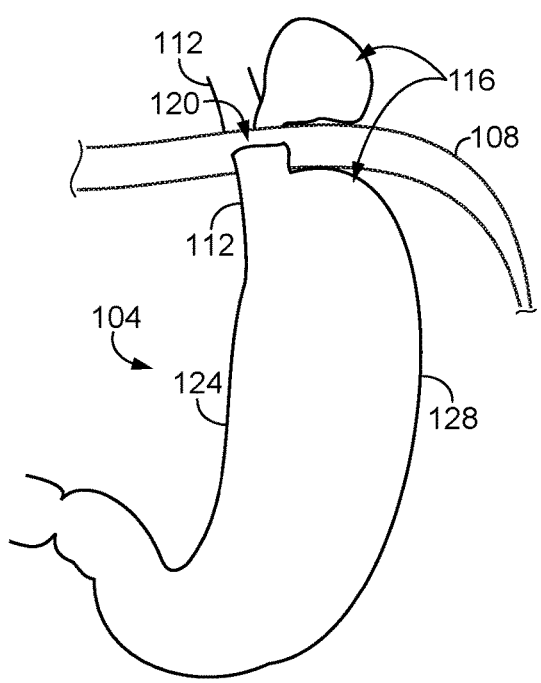
FIG. 3 is an anterior view of an exemplary abdominal region of a patient in a herniated condition.

In an early stage condition, the greater curve 128 at the fundus 116 forms a generally obtuse angle where the greater curve 128 meets the esophagus 112. The same is illustrated in the exemplary anterior view of the abdominal area shown in FIG. 2. In an early stage condition, the stomach 104 slides upward toward the diaphragm 108 but remains below the diaphragm.

In a herniated condition, a portion of the stomach 104, such as the fundus 116, may slide through the hiatus 120 and into the chest. This may be caused by a tear or weakness of the hiatus 120 of the diaphragm 108. A patient may experience chest pain, heartburn or both. In serious cases, blood flow to the stomach 104 may be strangled or limited.

In such cases, surgery may be recommended to repair or reduce the hernia. In addition, in early stage conditions, surgery may be utilized to decrease or reinforce the hiatus 120 to prevent a hiatal hernia from forming or enlarging.

One cause of hiatal hernias is obesity. As such, patients undergoing gastric surgery may also undergo an improved hiatal hernia treatment where by the hiatus 120 is reinforced or otherwise repaired, a hiatal hernia is reduced or repaired, or both as appropriate when an early stage condition or herniated condition is detected.

Figure 4:
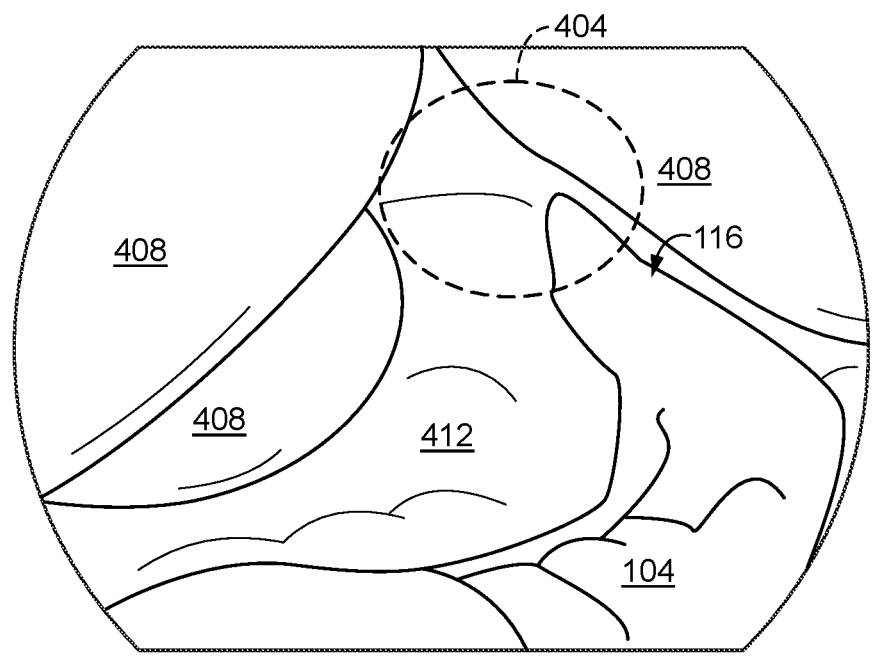
FIG. 4 is an anterior perspective view of an exemplary abdominal region of a patient and area of repair.

Referring to FIG. 4, which illustrates an anterior view of an exemplary abdominal region as may be seen from a laparoscope, the stomach 104 may be surrounded and connected to other portions of the abdominal region via connective tissue 412. Connective tissue may comprise fat, blood vessels and other structures.

The area of repair 404 shown is below the lungs 408 and adjacent the fundus 116 of the stomach 112. In one or more embodiments, the area of repair 404 will be that containing the hiatus where it meets the esophagus. The connective tissue 412 surrounding the area of repair 404 must be dissected, divided, or both to expose the hiatus and esophagus. Dissection may be accomplished with various laparoscopic instruments. Typically, this area of a patient contains significant amounts of connective tissue 412 which must be dissected or divided before a hiatal hernia can be repaired. This causes trauma to the area.

It is noted that the area of repair 404 may differ, such as by being larger or smaller, for different patients. In addition, more extensive dissection may occur to access the area of repair 404 in some cases. For example, dissection may occur further into the chest cavity, superior to the diaphragm or area of repair 404. As will be discussed below, such dissection may be treated as part of the improved hiatal hernia treatment disclosed herein to aid in patient recovery.

Figure 5:
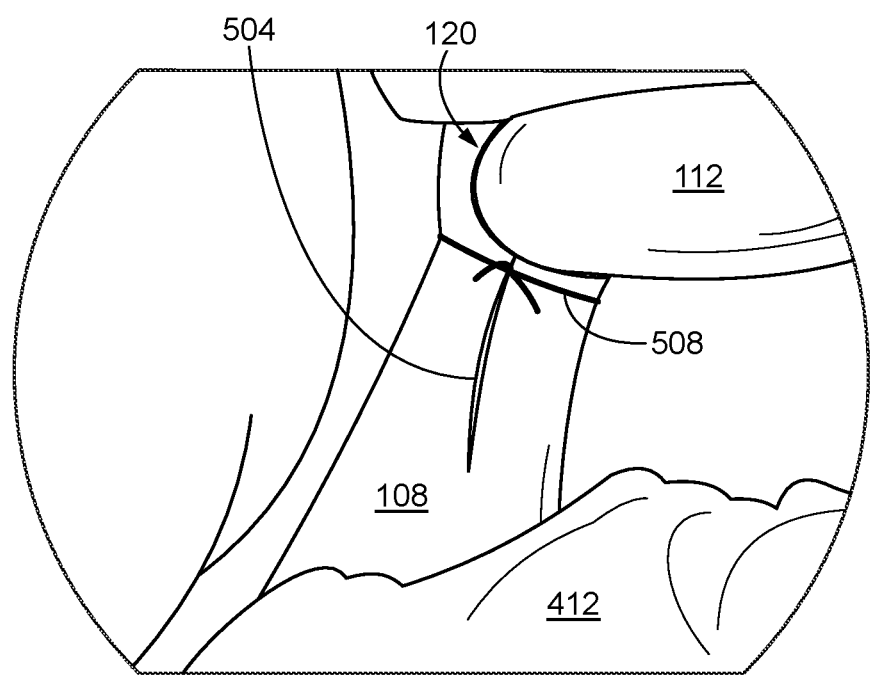
FIG. 5 is an anterior perspective view of an exemplary area of repair with a treated hiatal hernia.

An exemplary area of repair after dissection is shown in FIG. 5. The connective tissue 412 has been dissected or divided sufficient to reveal the diaphragm 108, hiatus 120, and esophagus 112. As can be seen, a tear 504 is adjacent the hiatus 120 which would allow the stomach to enter or pass through the hiatus, creating a hernia. However, as shown, the esophagus 112 and stomach have been positioned, such as shown in the normal condition of FIG. 1, and the hiatus 120 has been reinforced by tying surgical suture 508 to prevent the stomach from sliding or otherwise moving into or through the hiatus.

Though illustrated as a posterior repair procedure in FIG. 5, it is noted that various repair procedures may be utilized. For example, repair may occur from an anterior position in some embodiments.

Figure 6:
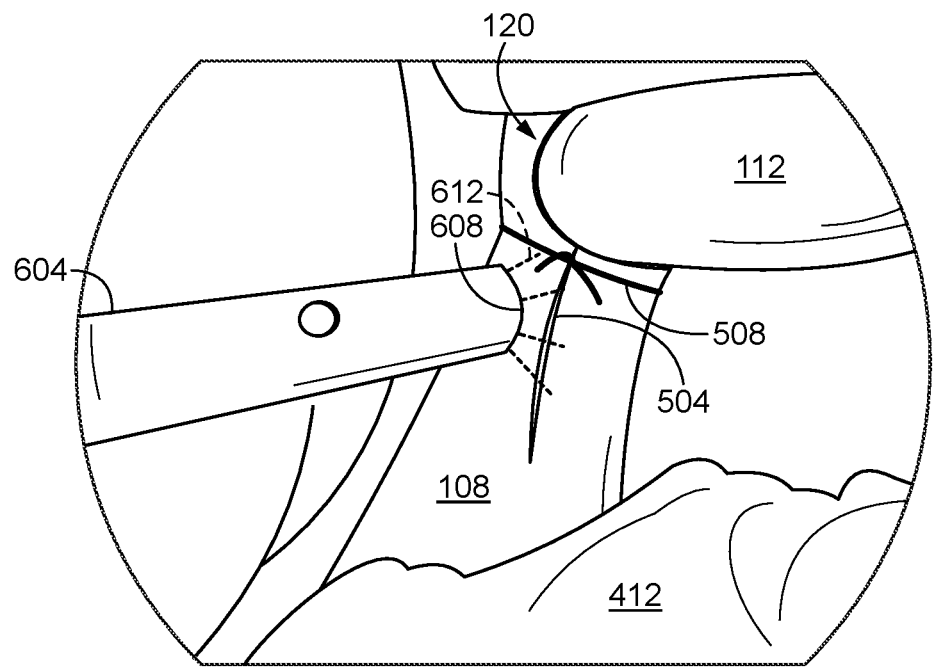
FIG. 6 is an anterior perspective view of an exemplary area of repair undergoing application of anesthesia.
Figure 7:
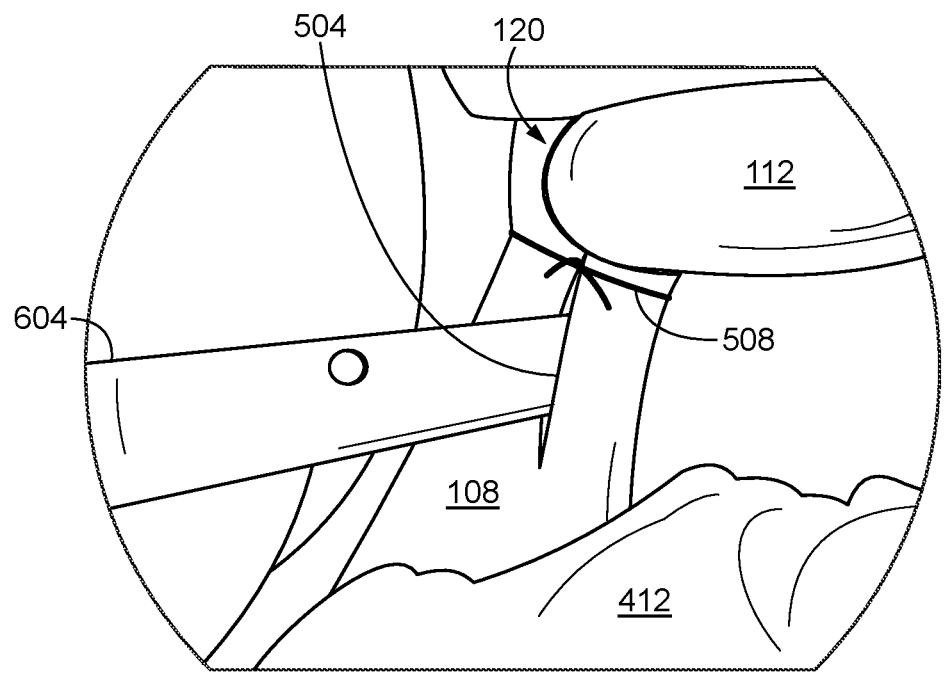
FIG. 7 is an anterior perspective view of an exemplary area of repair undergoing application of anesthesia.

FIGS. 6 and 7 illustrate application of anesthesia at the area of repair via an applicator 604. As can be seen, anesthetic 612 may be applied to various surfaces in an area of repair by an applicator 604. In FIGS. 6 and 7 for example, the applicator 604 allows a fluidic flow of anesthetic 612 to flow onto and coat internal and external surfaces of the hiatus 120 and diaphragm 108. In FIG. 6, the applicator 604 applies anesthetic 612 to an external surface of the diaphragm 108 and hiatus 120 where the surgical suture 508 has been added.

An open end, outlet, or nozzle 608 of the applicator 604 may be used to control the locations at which anesthetic 612 is applied. For example, FIG. 7 illustrates that the applicator 604 may apply anesthetic to an interior surface of the hiatus 120, such as by insertion of the applicator's nozzle 608 into the hiatus 120 or tear 504. In addition, an applicator 604 may increase or decrease the flow rate of anesthetic 612 as desired such as by constricting or expanding a valve or the like thereof.

As alluded to in the foregoing, an applicator 604 may comprise a tubular structure in fluid communication with a reservoir or source holding a quantity of anesthetic 612. In use, the anesthetic 612 may flow from the reservoir and through the applicator 604 where it may be applied to a surface via the nozzle 608 of the applicator. It is noted that, typically, an applicator 604 will not inject or otherwise pressurize the anesthetic 612 but rather the anesthetic will be driven by gravity out of the applicator's nozzle 608 and onto the desired surface or surfaces.

Application of anesthetic 612 reduces pain at the area of repair for a number of hours after the improved hiatal hernia treatment is completed. In some cases, pain can be reduced for approximately six hours after the improved hiatal hernia treatment is completed. The period of time immediately after a surgical procedure is typically the most painful for patients. Reduction of pain is beneficial in lowering patient stress, discomfort, and heartrate, especially during the postoperative period. In addition, the need for postoperative pain medication, and during the perioperative period overall, is typically reduced as compared to traditional procedures.

Figure 8:
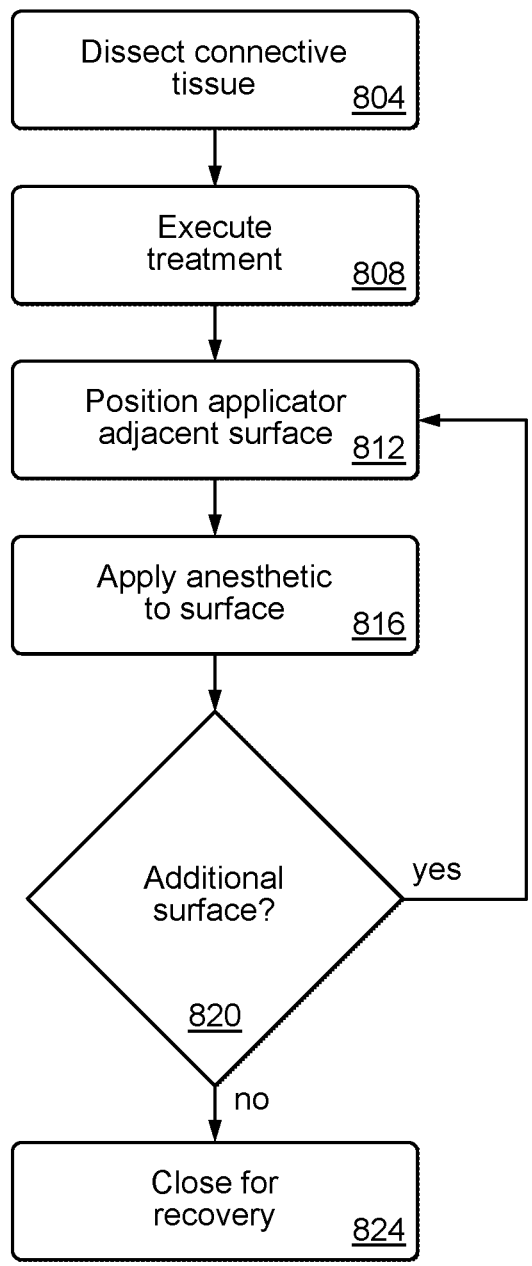
FIG. 8 is a flow diagram illustrating an exemplary improved hiatal hernia treatment.

The improved hiatal hernia treatment will now be described with respect to the exemplary flow diagram of FIG. 8. At a step 804, the connective tissue surrounding an area of repair may be divided or otherwise dissected with one or more laparoscopic or other surgical instruments. For instance, as described above, fatty tissue and blood vessels connected to the esophagus, stomach, and diaphragm may be dissected to expose the area of repair.

At a step 808, a treatment may be executed. In one or more embodiments, the treatment reinforces the hiatus to prevent a hernia from forming or enlarging. A treatment may include repositioning a herniated stomach. A surgical suture, staples, or other reinforcement devices may be sewn, tied, or otherwise implanted to reinforce or repair the hiatus.

After treatment is completed, an applicator may be positioned adjacent a surface at a step 812, such as a surface of the hiatus, diaphragm, or other adjacent structure. The applicator will typically be positioned such that its nozzle is adjacent the surface. At a step 816 anesthetic may be applied to the selected surface, such as by permitting the anesthetic to flow out of the applicator's nozzle. This coats the surface with anesthetic thereby numbing the surface to pain.

At a decision step 820, additional surfaces may have anesthetic applied thereto such as by returning to step 812 to position the applicator adjacent another surface. As illustrated in FIGS. 6 and 7 for instance, anesthetic is applied an interior surface of the hiatus as well as an exterior surface of the hiatus. Anesthetic may be applied to one or more dissected areas as well, including any dissections superior to or otherwise adjacent to an area of repair. As can be seen, this process may be repeated one or more times to apply anesthetic to other organ surfaces within or adjacent the area of repair.

Once all desired surfaces have had anesthetic applied thereto, the patient may be closed for recovery at a step 824, such as by removing any instrumentation, pads, or other surgical implements and closing incisions with staples, sutures, or the like. The patient can then proceed to the postoperative recovery stage. As can be seen, the application of anesthetic may be specific to the area of repair, where the patient is likely to experience the most pain after surgery. This is advantageous in reducing the need for other pain medication as while improving patient comfort and heart rate, thereby enhancing the recovery process.

Though described herein with regard to hiatal hernia treatments, it is contemplated that anesthetic may be applied as described herein during a variety of surgeries to directly address pain at various areas of repair. Typically, anesthetic will be applied after a treatment but prior to completion of the treatment (i.e., the end of the surgical procedure). It is contemplated though that, in some embodiments, anesthetic may be applied to an area of repair during the postoperative period, such as by introducing an applicator laparoscopically and applying anesthetic to one or more surfaces, as disclosed herein.

Figure 9:
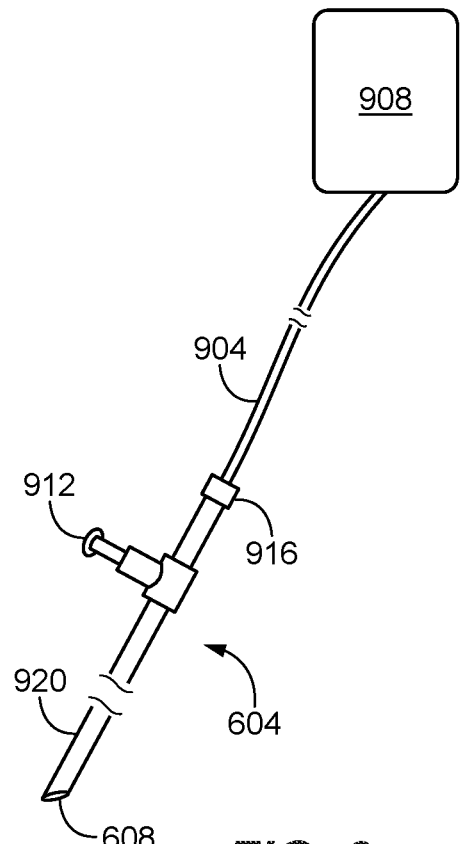
FIG. 9 illustrates an exemplary applicator.

In one or more embodiments, an applicator 604 will be a laparoscopic instrument to permit use while minimizing the size of incisions in the patient. An exemplary applicator 604 is shown in FIG. 9. As can be seen, an applicator may comprise an inlet 916 and a nozzle 608 or outlet. A tubular shaft or body 920 may extend between an inlet 916 and nozzle 608. In one or more embodiments, the body 920 may be rigid and extend various lengths, as indicated in FIG. 9.

As disclosed above, in operation, the nozzle 608 of an applicator 604 may be positioned adjacent a selected surface. Thereafter, anesthetic may flow through the applicator 604 and out the nozzle 608 for application to the surface. The flow rate may be controlled by a valve 912 or the like of the applicator 604.

One or more reservoirs 908 may be provided to hold anesthetic. A conduit 904 may connect the inlet 916 of an applicator 604 to the reservoir 908 to allow the applicator to receive anesthetic therefrom. The conduit 904 will typically be flexible to allow free movement of the applicator 604, such as to position the nozzle 608 adjacent a selected surface.

While various embodiments of the invention have been described, it will be apparent to those of ordinary skill in the art that many more embodiments and implementations are possible that are within the scope of this invention. In addition, the various features, elements, and embodiments described herein may be claimed or combined in any combination or arrangement.

What is claimed is:

1. A method for a hiatal hernia treatment, the method comprising:
   exposing an area of repair containing a hiatal hernia;
   positioning one or more applicators at a hiatus within the area of repair;
   applying an anesthetic at distinct portions of the hiatus with the one or more applicators without pressurization to coat a surface of the hiatus;
   positioning the one or more applicators at an additional surface within or adjacent to the area of repair; and
   applying the anesthetic to the additional surface.

2. The method of claim 1, further comprising adjusting a valve of the one or more applicators.

3. The method of claim 1, wherein the application of the anesthetic to coat the surface of the hiatus is gravity driven.

4. The method of claim 1, wherein a nozzle of the one or more applicators is adjacent the hiatus when the anesthetic is applied to coat the surface of the hiatus.

5. The method of claim 1, wherein a nozzle of the one or more applicators is within the hiatus when the anesthetic is applied to coat the surface of the hiatus.

6. The method of claim 1, wherein:
   the additional surface is a portion of a diaphragm within the area of repair.

7. The method of claim 1, wherein:
   the additional surface is a portion of an esophagus within the area of repair.

8. A method for a hiatal hernia treatment, the method comprising:
   exposing an area of repair containing a hiatal hernia;
   positioning one or more applicators at a hiatus, the one or more applicators comprising a reservoir holding an anesthetic and one or more valves;
   opening the one or more valves to provide a flow of the anesthetic from the reservoir, wherein the flow of the anesthetic is gravity driven;
   applying the flow of the anesthetic to distinct portions proximate the hiatus with the one or more applicators to coat a surface of the hiatus;
   positioning the one or more applicators at an additional surface within or adjacent to the area of repair; and
   applying the anesthetic to the additional surface.

9. The method of claim 8, wherein a nozzle of the one or more applicators is adjacent the hiatus when the anesthetic is applied to coat the surface of the hiatus.

10. The method of claim 8, wherein a nozzle of the one or more applicators is within the hiatus when the anesthetic is applied to coat the surface of the hiatus.

11. The method of claim 8, wherein:
    the additional surface is a portion of a diaphragm within the area of repair.

12. The method of claim 8, wherein:
    the additional surface is a portion of an esophagus within the area of repair.

13. The method of claim 8, further comprising closing the area of repair subsequent to the application of the flow of the anesthetic to coat the surface of the hiatus.

* * * * *